US009057094B1

(12) United States Patent
Perez et al.

(10) Patent No.: US 9,057,094 B1
(45) Date of Patent: Jun. 16, 2015

(54) NANOPARTICLE-MEDIATED METHODS FOR ANTIMICROBIAL SUSCEPTIBILITY TESTING OF BACTERIA

(75) Inventors: J. Manuel Perez, Orlando, FL (US); Charalambos Kaittanis, Orlando, FL (US); Sudip Nath, Orlando, FL (US)

(73) Assignees: UNIVERSITY OF CENTRAL FLORIDA RESEARCH FOUNDATION, INC., Orlando, FL (US); NATIONAL INSTITUTES OF HEALTH (NIH), U.S. DEPT. OF HEALTH AND HUMAN SERVICES (DHHS, Bethesda, MD (US)

( * ) Notice: Subject to any disclaimer, the term of this patent is extended or adjusted under 35 U.S.C. 154(b) by 1233 days.

(21) Appl. No.: 12/258,785

(22) Filed: Oct. 27, 2008

Related U.S. Application Data

(60) Provisional application No. 60/982,529, filed on Oct. 25, 2007.

(51) Int. Cl.
*C12Q 1/18* (2006.01)
*B82Y 30/00* (2011.01)
*A61K 49/18* (2006.01)

(52) U.S. Cl.
CPC . *C12Q 1/18* (2013.01); *B82Y 30/00* (2013.01); *A61K 49/1821* (2013.01)

(58) Field of Classification Search
None
See application file for complete search history.

(56) References Cited

U.S. PATENT DOCUMENTS

| | | | |
|---|---|---|---|
| 5,660,990 A | | 8/1997 | Rao |
| 5,770,388 A | * | 6/1998 | Vorpahl ................ 435/7.25 |
| 6,661,221 B2 | | 12/2003 | Taguchi |
| 6,891,368 B2 | | 5/2005 | Kawano |
| 7,531,149 B2 | | 5/2009 | Peng |
| 8,409,463 B1 | | 4/2013 | Perez |
| 2002/0151787 A1 | | 10/2002 | Bjornerud |
| 2003/0124194 A1 | | 7/2003 | Gaw |
| 2004/0086885 A1 | | 5/2004 | Lee |
| 2006/0275757 A1 | | 12/2006 | Lee |
| 2006/0286379 A1 | | 12/2006 | Gao |
| 2007/0090323 A1 | | 4/2007 | Duguet |
| 2010/0072994 A1 | | 3/2010 | Lee |
| 2011/0021374 A1 | | 1/2011 | Lee |
| 2013/0330280 A1 | | 12/2013 | Perez |

FOREIGN PATENT DOCUMENTS

| | | |
|---|---|---|
| EP | 1260595 | 11/2002 |
| EP | 0805343 | 7/2003 |
| EP | 1458031 | 1/2005 |
| EP | 1631318 | 11/2010 |
| WO | WO 03/072830 | 9/2003 |
| WO | WO 2004/003508 | 1/2004 |
| WO | WO 2009/085214 | 7/2009 |
| WO | WO 2012/159121 | 11/2012 |

OTHER PUBLICATIONS

Skrivanova et al. Veterinarni Medicina, 2006, 51(3): 81-88.*
Aslan et al. "Nanogold-plasmon-resonance glucose sensing". Analytical Biochemistry. 2004, 330, pp. 145-155.*
Kaittanis et al. "One-step, nanoparticle-mediated bacterial detection with magnetic relaxation". Nano Lett. 2007, 7(2), pp. 380-383.*
Behrens et al. Journal of Physics: Condensed Matter 18 (2006), S2543-S2561.*
Baghi M, et al. (2005) The efficacy of MRI with ultrasmall superparamagnetic iron oxide particles (USPIO) in head and neck cancers. Anticancer Res. 25: 3665-3670.
Corr SA, et al. (2008) From Nanocrystals to Nanorods: New Iron Oxide—Silica Nanocomposites from Metallorganic Precursors. 112: 1008-1018.
Culp JT, et al. (2003) Monolayer, bilayer, multilayers: evolving magnetic behavior in Langmuir-Blodgett films containing a two-dimensional iron-nickel cyanide square grid network. Inorg Chem. 42: 2842-2848.
Enpuka K. (2005) Magnetic immunoassay with SQUID and magnetic marker. Digests of the IEEE International. 413-415.
Fazzina D. (2007) 7347-Facile Synthesis of Highly Magnetic Polymer Coated Iron Oxide Particles for Sensing Applications. NERAC, Inc. Research Report No. 10032825 (Tolland, CT) (2 pages).
Fujii T, et al. (1999) In situ XPS analysis of various iron oxide films grown by NO2-assisted molecular-beam epitaxy. Phys Rev. 59: 3195-9202.
Gao LZJ, et al. (2007) Intrinsic peroxidase-like activity of ferromagnetic nanoparticles. Nat Nanotechnol. 2: 577-583.
Gass J, et al. (2006) Superparamagnetic Polymer Nanocomposites with Uniform Fe3O4 Nanoparticle Dispersions. Advanced Functional Materials. 16: 71-75.
Goya GFB, et al. (2003) Static and dynamic magnetic properties of spherical magnetite nanoparticles. J Appl Phys. 94: 3520.
Gupta AK and Curtis AS. (2004) Surface modified superparamagnetic nanoparticles for drug delivery: interaction studies with human fibroblasts in culture. J Mater Sci Mater Med. 15: 493-496.
Gupta AK, et al. (2005) Synthesis and surface engineering of iron oxide nanoparticles for biomedical applications. Biomaterials. 26: 3995-4021.

(Continued)

*Primary Examiner* — Vera Afremova
(74) *Attorney, Agent, or Firm* — Ballard Spahr LLP

(57) ABSTRACT

A method of testing bacterial cells for antimicrobial susceptibility includes preparing a suspension of the bacterial cells in a non-nutrient medium, mixing with the suspension an antimicrobial, a carbohydrate usable by the bacterial cells, metallic nanoparticles, and a lectin, and incubating the mixture while monitoring a parameter of the nanoparticles responsive to use of the carbohydrate by the bacterial cells. More broadly stated, the invention includes a method of testing an agent for its effect on cell metabolism by preparing a suspension of cells in a non-nutrient medium, mixing the suspension with the agent, adding a carbohydrate usable by the cells, metallic nanoparticles, and a lectin with binding specificity for the added carbohydrate, and monitoring a nanoparticle parameter responsive to the cells.

13 Claims, 13 Drawing Sheets

(56) References Cited

OTHER PUBLICATIONS

Hellstern D, et al. (2006) Systemic distribution and elimination of plain and with Cy3.5 functionalized poly(vinyl alcohol) coated superparamagnetic maghemite nanoparticles after intraarticular injection in sheep in vivo. J Nanosci Nanotechnol. 6: 3261-3268.

Hu J, et al. (2001) Linearly polarized emission from colloidal semiconductor quantum rods. Science. 292: 2060-2063.

Ito A, et al. (2004) Magnetite nanoparticle-loaded anti-HER2 immunoliposomes for combination of antibody therapy with hyperthermia. Cancer Lett. 212: 167-175.

Jaiswal JK, et al. (2004) Synaptotagmin VII restricts fusion pore expansion during lysosomal exocytosis. PLoS Biol. 2: E233.

Jiang W, et al. (2004) Preparation and properties of superparamagnetic nanoparticles with narrow size distribution and biocompatible. Journal of Magnetism and Magnetic Materials. 283: 210-214.

Josephson L, et al. (1999) High-efficiency intracellular magnetic labeling with novel superparamagnetic-Tat peptide conjugates. Bioconjug Chem. 10: 186-191.

Jun Y, et al. (2005) Nanoscale size effect of magnetic nanocrystals and their utilization for cancer diagnosis via magnetic resonance imaging. J Am Chem Soc. 127: 5732-5733.

Kaittanis C, et al. (2007) One-step, nanoparticle-mediated bacterial detection with magnetic relaxation. Nano Lett. 7: 380-383.

Kaittanis C, et al. (2012) Rapid and sensitive detection of an intracellular pathogen in human peripheral leukocytes with hybridizing magnetic relaxation nanosensors. PLoS One. 7(4):e35326.

Kohler N, et al. (2005) Methotrexate-modified superparamagnetic nanoparticles and their intracellular uptake into human cancer cells. Langmuir. 21: 8858-8864.

Lee H, et al. (2006) Antibiofouling polymer-coated superparamagnetic iron oxide nanoparticles as potential magnetic resonance contrast agents for in vivo cancer imaging. J Am Chem Soc. 128: 7383-7389.

Li W, et al. (2006) Multiamino-functionalized carbon nanotubes and their applications in loading quantum dots and magnetic nanoparticles. J Mater Chem. 16: 1852-1859.

Magana D, et al. (2006) Switching-on superparamagnetism in Mn/CdSe quantum dots. J Am Chem Soc. 128: 2931-2939.

Manna LS, et al. (2000) Synthesis of Soluble and Processable Rod-, Arrow-, Teardrop-, and Tetrapod-Shaped CdSe Nanocrystals. J. Am. Chem. Soc. 122: 12700-12706.

Melosh NA, et al. (2003) Ultrahigh-density nanowire lattices and circuits. Science. 300: 112-115.

Nath S, et al. (2009) Synthesis, magnetic characterization and sensing applications of novel dextran-coated iron oxide nanorods. Chem Mater. 21(8): 1761-1767.

Nath S, et al. (2008) Dextran-coated gold nanoparticles for the assessment of antimicrobial susceptibility. Anal Chem. 80: 1033-1038.

Nedeljkovic D, et al. (2004) Application of Permanent Magnetic Powder for Magnetic Field Sensing Elements. Rom Journ Phys. 50: 971-976.

Park SJ, et al. (2000) Synthesis and Magnetic Studies of Uniform Iron Nanorods and Nanospheres. J Am Chem Soc. 122: 8581-8582.

Peng X, et al. (2000) Shape control of CdSe nanocrystals. Nature. 404: 59-61.

Perez JM, et al. (2002a) Magnetic relaxation switches capable of sensing molecular interactions. Nat Biotechnol. 20: 816-820.

Perez JM, et al. (2002b) DNA-based magnetic nanoparticle assembly acts as a magnetic relaxation nanoswitch allowing screening of DNA-cleaving agents. J Am Chem Soc. 124: 2856-2857.

Perez JM, et al. (2003) Viral-induced self-assembly of magnetic nanoparticles allows the detection of viral particles in biological media. J Am Chem Soc. 125: 10192-10193.

Perez JM, et al. (2004) Use of magnetic nanoparticles as nanosensors to probe for molecular interactions. Chembiochem. 5: 261-264.

Perez JM, et al. (2008) Synthesis of biocompatible dextran-coated nanoceria with pH-dependent antioxidant properties. Small. 4: 552-556.

Perez JM. (2007) Iron oxide nanoparticles: hidden talent. Nat Nanotechnol. 2: 535-536.

Puntes VF, et al. (2001) Colloidal nanocrystal shape and size control: the case of cobalt. Science. 291: 2115-2117.

Radojevic V, et al. (2004) Process of Coating Optical Fiber with Composite Coating: Composite Coating: Magnetic Powder—Polymer. Powder metallurgy; Euro PM2004. 533-538.

Shen T, et al. (1993) Monocrystalline iron oxide nanocompounds (MION): physicochemical properties. Magn Reson Med. 29: 599-604.

Thorek DL, et al. (2006) Superparamagnetic iron oxide nanoparticle probes for molecular imaging. Ann Biomed Eng. 34: 23-38.

Wang DH, et al. (2004) Superparamagnetic $Fe_2O_3$ Beads—CdSe/ZnS Quantum Dots Core—Shell Nanocomposite Particles for Cell Separation. Nano Lett. 4: 409-413.

Wang JP, et al. (2004) Growth of magnetite nanorods along its easy-magnetization axis of [1 1 0]. J Cryst Growth. 263: 616-619.

Zhao YM, et al. (2006) Growth and characterization of iron oxide nanorods/nanobelts prepared by a simple iron-water reaction. Small. 2: 422-427.

Zou G, et al. (2005) $Fe_3O_4$ nanocrystals with novel fractal. J Phys Chem B. 109: 18356-18360.

International Preliminary Report on Patentability issued Nov. 28, 2013 for PCT Application No. PCT/US2012/038903 filed May 21, 2012 and published as WO 2012/159121 on 11/122/2012 (Inventors—Perez et al. // Applicant—University of Central Florida Research Foundation) (5 pages).

International Search Report issued Jan. 28, 2013 and published as WO 2012/159121 on 11/122/2012 (Inventors—Perez et al. // Applicant—University of Central Florida Research Foundation) (4 pages).

Written Opinion issued Jan. 28, 2013 and published as WO 2012/159121 on 11/122/2012 (Inventors—Perez et al. // Applicant—University of Central Florida Research Foundation) (4 pages).

* cited by examiner

NANOPARTICLE-MEDIATED METHODS FOR ANTIMICROBIAL SUSCEPTIBILITY TESTING OF BACTERIA

RELATED APPLICATION

This application claims priority from co-pending provisional application Ser. No. 60/982,529, which was filed on 25 Oct. 2007, and which is incorporated herein by reference in its entirety.

STATEMENT REGARDING FEDERALLY SPONSORED RESEARCH

This invention was made with government support under K01 CA101781 awarded by the National Institutes of Health. The government has certain rights in the invention.

FIELD OF THE INVENTION

The present invention relates to the field of infectious diseases and, more particularly, to methods of determining the susceptibility of cells, particularly bacterial cells, to a potential treatment agent such as an antibiotic.

BACKGROUND OF THE INVENTION

The identification and administration of an effective antimicrobial agent is of the utmost importance in clinical and point-of-care patient settings. Specifically, with the emergence of multi-drug resistant bacterial strains, such as methicillin-resistant Staphylococcus aureus (MRSA) and multiply drug resistant tuberculosis (XDR-TB), identifying the most effective antibiotic and administering it to the patient at concentrations that will kill or inhibit bacterial growth without undermining the patient's health is important.

Currently, the assessment of antimicrobial susceptibility relies on the isolation of the microorganism, followed by an attempt to grow the pathogen in the presence of various antibiotic agents and different concentrations thereof. A major problem with this approach is that it requires at least 24 hours in order to provide qualitative and quantitative information associated with the effectiveness of the antibitiotic. In the meantime, even though physicians will institute treatment on clinical grounds and without waiting for the lab results, the patient might face severe complications and worsening of his/her pathological condition due to growth and pathogenesis induced by the microorganism and inability of the immune system to respond in an effective way. As mentioned before, typically, physicians caring for the hospitalized patient must start antibiotic treatment based only on experience and clinical hunches, since the results of in vitro antibiotic susceptibility tests will not be available for 48-72 hours after initial cultures are taken.

Therefore, the need of fast and accurate antimicrobial susceptibility assessment modalities remains, even in this day of modern medical advances. Additionally, apart from clinical and point-of-care diagnostics, the pharmaceutical industry is under pressure to continue development of novel, sensitive and rapid antimicrobial susceptibility assays. Hence, having methods to facilitate high-throughput screening of candidate antibiotics, while using small sample volumes, could reduce the costs associated with drug development and expedite the drug development process.

SUMMARY OF THE INVENTION

With the foregoing in mind, the present invention advantageously provides a novel, rapid and sensitive method for testing the effect of a treatment agent upon a cell's metabolism. The methods of the invention are eminently applicable to antibiotic susceptibility testing of bacterial isolates. Additionally, the disclosed methods may also be employed to test an agent for its effect on the metabolism of cells, whether the cells are bacterial cells or the cells of higher organisms, including mammalian cells in culture.

Significant efforts have been made for the development of biosensors, capable of detecting biological targets, such as proteins, nucleic acids, viruses and bacteria. The aggregation of metallic nanoparticles, induced by specific biomolecular interactions, has been employed in the development of simple and sensitive biosensors with potential applications in immunoassays. Noble metal nanoparticles, in particular gold nanoparticles (AuNPs), have recently been the focus of extensive studies in this field, due to their extraordinary optical and electronic properties.

Gold nanoparticles exhibit a strong surface plasmon resonance band, as a consequence of collective oscillations of the surface electrons, which are induced by the incident electromagnetic radiation. On the other hand, iron-oxide-based magnetic nanocrystals have been widely used in a variety of biomedical applications, for example, in diagnostics, magnetic resonance imaging (MRI) and magnetically-guided site-specific drug delivery systems. Notably, the use of magnetic nanoparticles in the fast and reliable detection of a specific bacterium in complex biological media (blood and milk) has been recently reported.

The working mode of these nanosensors relies on the phenomenon where in the presence of a target these nanosensors self-assemble, that is, they agglutinate. The induction of nano-assembly formation results in a concomitant significant change in the surface plasmon resonance of noble metal nanoparticles (either gold or silver). In the case of magnetic nanoparticles (such as iron oxide), there is a dramatic effect on the spin-spin relaxation time (T2) of neighboring water molecules' protons.

Based on the above behavior, we have developed a quick and facile assay for the assessment of antimicrobial susceptibility, using either gold or iron oxide nanoparticles (IONPs) coated with a polysaccharide layer preferably but not exclusively composed of polymerized dextran. Particularly, the detection principle relies on the fact that in the presence of an effective antibiotic (bactericidal or bacteriostatic) and at inhibitory concentrations, there is suppression of the bacterial metabolism and reduction in nutrient uptake (i.e. carbohydrates). Hence, the concentration of the nutrients, such as starch and other carbohydrates, remains higher when compared to those under non-inhibitory antibiotic concentrations, antibiotic resistance, antibiotic incompetence or absence of an inhibitory compound. Therefore, after incubating the nanoparticle-specimen suspension in the presence of Concanavalin A (Con A), it is possible to assess the metabolic activity of the cells, based on the concentration of carbohydrate remaining, which is related to the changes in T2 or surface plasmon resonance band.

The presently described methods have several advantages over existing methodology. The present methods are facile and cost effective. Preparation of the nanoparticles does not require the use of toxic reagents, and therefore the synthesized nanoparticles are environmentally friendly and non-toxic to the assay's user. Good stability of the resulting particles over prolonged storage in water, phosphate buffered saline and citrate buffer, makes them suitable for use at the points-of-care and under harsh conditions. The resulting gold and iron oxide particles can be concentrated using ultrafiltration devices without inducing agglomeration of the nanoparticles. Polysaccharide-coated gold and iron oxide nanoparticles can be used to assess bacterial metabolism fast and accurate with available instrumentation, based on the consumption of carbohydrates in the culture medium. Dextran-coated gold and iron oxide nanoparticles can be used to assess antimicrobial susceptibility and an antibiotic's minimum inhibitory concentration (MIC), based on the consumption of carbohydrates by the microorganisms, without relying on the expression of reporter genes. Dextran-coated gold and iron oxide nanoparticles can fast and reliably assess the state of bacterial metabolism and antimicrobial susceptibility, requiring a fraction of the time needed by such standard methods as the turbidity test, disc diffusion assay, and plate growth). Dextran-coated gold and iron oxide nanoparticles can determine bacterial metabolism and antimicrobial susceptibility using small sample volumes (about 10 µL), which is useful for the screening of expensive antimicrobial agents and growth in specialized culture media.

Dextran-coated gold and iron oxide nanoparticles can assess antimicrobial susceptibility in an affordable, high-throughput setting, supporting expedited decision making. The nanoparticles of the present invention can be used in the field and at the point-of-care to assess antimicrobial susceptibility, as they are stable over a wide range of temperatures and do not require special storage conditions. The dextran-coated nanoparticles can determine antimicrobial susceptibility using bacteria isolated from clinical and environmental specimens, without the need to use engineered or sensitive strains. The dextran-coated nanoparticles can facilitate antimicrobial susceptibility, without the use of radioactive or hazardous materials. etermination of antimicrobial activity can be performed with either a simple UV-Vis spectrophotometer or a miniaturized, portable NMR, using gold and iron oxide nanoparticles respectively.

Accordingly, the present invention provides a method of testing bacterial cells for antimicrobial susceptibility. The method comprises preparing a suspension of the bacterial cells in a non-nutrient medium and mixing with the suspension an antimicrobial, a carbohydrate usable by the bacterial cells, metallic nanoparticles, and a lectin. The method continues by incubating the mixture while monitoring a parameter of the nanoparticles responsive to use of the carbohydrate by the bacterial cells.

More broadly stated, the invention discloses a method of testing an agent for its effect on cell metabolism. This embodiment of the invention includes preparing a suspension of cells in a non-nutrient medium, mixing the suspension with the agent, adding a carbohydrate usable by the cells, metallic nanoparticles, and a lectin with binding specificity for the added carbohydrate, and monitoring a nanoparticle parameter responsive to the cells.

Yet another variation in the present invention includes a method of monitoring the metabolism of cells. This method comprises preparing a suspension of the cells in a non-nutrient medium, mixing the suspension with metallic nanoparticles bearing a lectin, adding to the suspension a carbohydrate metabolizable by the cells and monitoring the nanoparticles for a parameter responsive to metabolism of the carbohydrate by the cells.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
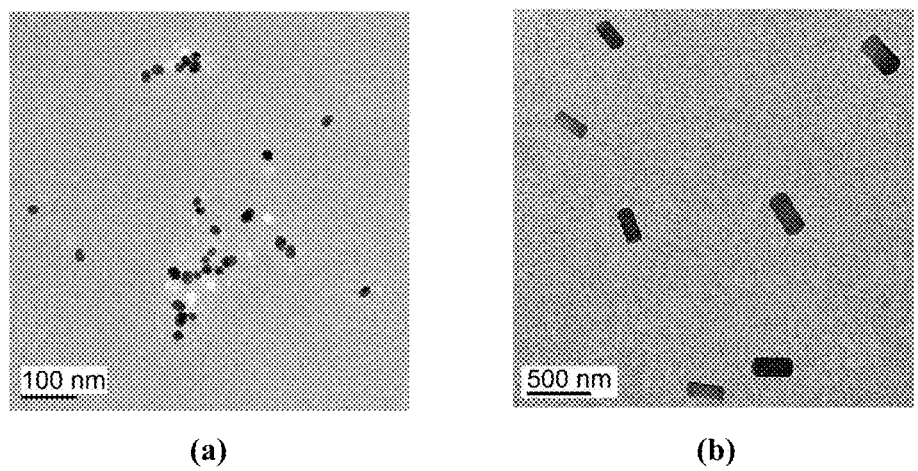
FIG. 1 is a TEM image of dextran-coated (a) gold and (b) iron oxide nanoparticles according to an embodiment of the present invention; the TEM images show that the gold nanoparticles are spherical, whereas the iron oxide particles are rods.
Figure 2:
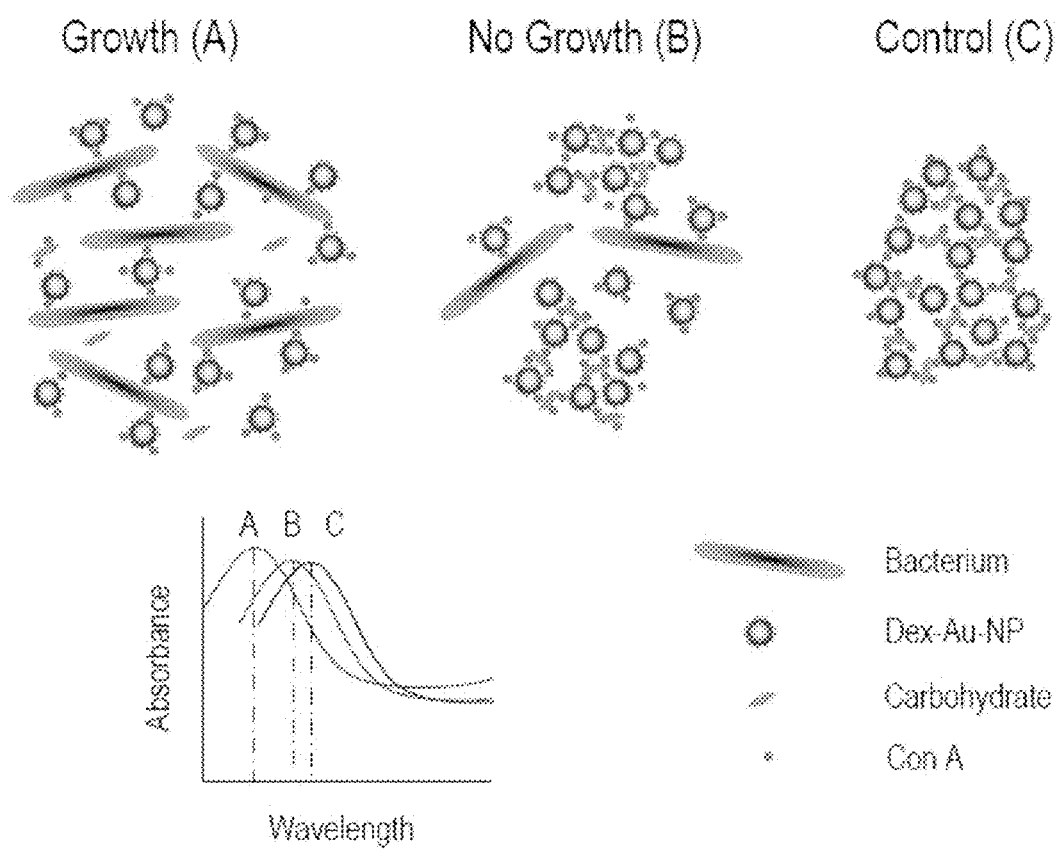
FIG. 2 shows a proposed model for gold nanoparticle (AuNP) mediated antimicrobial susceptibility assessment; in the absence of bacterial metabolism (B) or under sterile conditions (C), addition of Concanavalin A (ConA) results in the formation of extensive nanoassemblies and large shifts in the surface plasmon band of the AuNPs due to the contribution of free carbohydrates; bacterial metabolic activity is associated with lower shifts in the plasmonic band due to the formation of smaller nanoassemblies; the trend described herein is predicted to be similar when other metallic nanoparticles are used (for instance, silver) observing similar changes in surface plasmon peak; in addition, the same behavior is observed when magnetic polysaccharide-coated nanoparticles (such as iron oxide) are used, however in this case changes in water relaxation time are observed.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Portions of the disclosure made herein have been published in the scientific literature, as follows. Dextran-Coated Gold Nanoparticles for the Assessment of Antimicrobial Susceptibility; S. Nth, C. Kaittanis, A. Tinkham and J. M. Perez; *Analytical Chemistry*, 2008, 80, 1033-1038 (published on Web Jan. 17, 2008). Rapid Nanoparticle-Mediated Monitoring of Bacterial Metabolic Activity and Assessment of Antimicrobial Susceptibility in Blood with Magnetic Relaxation; C. Kaittanis, S. Nath and J. M. Perez; *Plos One*, September 2008, Vol. 3, Issue 9, e3253 (an Internet publication available at www.plosone.org). As noted above, both of these scientific articles are incorporated herein by reference in their entirety and are intended to constitute part of this disclosure.

Bacterial Cultures

In order to investigate if the dextran-coated iron oxide nanoparticles can monitor the starch utilization due to bacterial metabolic activity, different populations of *Escherichia coli* (strain 8739 from ATCC) were grown in starch-containing MH broth (DIFCOTM, BD) for 2 hours at 37° C. For determination of the minimum inhibitory concentration, *Escherichia coli* (106 CFU), *Serratia marcescens* (ATCC, 106 CFU) and *Shigella sonnie* (strain 9290 from ATCC, 106CFU) were grown in a starch-containing MH broth (DIFCOTM, BD), for 2 hours at 37° C. in the presence or absence of ampicillin. For determination of MIC in blood, bacterial stocks (106 CFU) were grown in the presence or absence of ampicillin in a 5%-blood-supplemented starch-containing MH broth, for 2 hours at 37° C. Defibrinated sheep blood was obtained from the Colorado Serum Company, simulating bacterial isolation and growth in typical blood agar plates. For studies requiring heat inactivation, *E. coli* bacteria wee autoclaved in the culture tubes for 10 minutes. Upon incubation or inactivation, all bacterial stocks were placed in a Fisher Isotemp freezer (Fisher Scientific, Hampton, N.H.), until further use.

Nanoparticle Synthesis

Reagents.

All the reagents used were of AR (Analytical Reagent) grade. Nitrogen-purged double-distilled water was used throughout the reaction. Iron salts, $FeCl_2.4H_2O$ and $FeCl_3.6H_2O$, were obtained from Fluka. Dextran (MW 10 kDa) was received from Amersham. TEOS: tetraethylorthosilicate (Fluka), APTS: 3-(amino-propyl)triethoxysilane (Aldrich) and THPMP: 3-(trihydroxysilyl)propylmethyl-phosphonate (Gelest Inc) were used as received from the suppliers.

Synthesis of Dextran-Coated Gold Nanoparticles (AuNPs):

Gold nanoparticles were synthesized by boiling a mixture of aqueous solution of gold chloride ($HAuCl_4$) and dextran (10 k). Explicitly, 1 ml $HAuCl_4$ ($10^{-2}$ M) was mixed with aqueous solution of dextran (10 g in 100 ml $H_2O$) and heated to boil on a hot plate. The solution turned pink within 10 min and exhibits a UV-visible band at 531 nm, attributed to the formation of gold nanoparticles. Finally, the gold nanoparticles were filtered and washed several times with distilled water through an Amicon cell (Millipore ultrafiltration membrane YM-30 k) to remove the free dextran molecules.

Synthesis of Aminated Silica Coated IO NPs:

The aminated silica-coated iron oxide nanoparticles were prepared using a previously published protocol, with modifications in order to yield stable nanoparticles via a water-based synthesis. Specifically, iron oxide nanocrystals were formed via the alkaline precipitation method, by mixing a solution of iron salts (0.202 g $FeCl_2.4H_2O$, 0.488 g $FeCl_3.6H_2O$, 88.7 μL HCl in 2 mL distilled water) with an ammonium hydroxide solution (830 μl $NH_4OH$ in 15 mL distilled water). Then, 20 seconds after the initiation of the iron oxide nanocrystal formation, a TEOS-THPMP-APTS solution was added (6180 μL THPMP, 2680 μL TEOS, 670 μL APTS) under continuous vortexing. The as-synthesized nanoparticle suspensions were centrifuged to remove large particles. Both the amino-silica- and dextran-coated nanoparticles were washed several times with distilled water and concentrated through an Amicon 8200 cell (Millipore Ultrafiltration membrane YM-30 k). Finally, the nanoparticle suspensions were stored at 4° C. until further use.

Concanavalin A was conjugated to the to aminated silica-coated iron oxide nanoparticles in the following manner. Two milliliters of aminated silica coated iron oxide nanoparticles (R2=225 $mM^{-1}s^{-1}$, [Fe]=0.47 mg/ml) were used for the conjugation of Con A to the nanoparticles' surface. Initially, in 1 mL of cold MES buffer (0.1 M, pH 6.0) 4.8 mg EDC (Pierce) and 3 mg NHS (Pierce) were dissolved. Then, 2 mg of lyophilized Con A (Type V, Sigma) were dissolved in 2 mL cold MES buffer (0.1 M, pH 6.0). Subsequently, the Con A solution was mixed with the EDC/NHS solution, followed by a 3-minute low-speed rotary mixing at room temperature. Finally, the aminated silica-coated iron oxide nanoparticles were added to the Con A (amine-reactive NHS-ester form) solution, followed by periodical rotary mixing at low speed and storage at 4° C. The resulting Con A-conjugated silica-coated iron oxide nanoparticles were purified from any unbound protein via magnetic separation using an MES buffer-equilibrated (0.1 M) LS25 MACSH column (Miltenyi Biotec).

Synthesis of Dextran-Coated IO Nanoparticles (IO NPs):

A mixture of iron salts 0.203 g $FeCl_2.4H_2O$ and 0.488 g $FeCl_3.6H_2O$ in HCl solution (88.7 μl 12 N HCl in 2 ml water) was added to $NH_4OH$ (830 μl in 15 ml $N_2$ purged deionized water) and stirred on a digital vortex mixer for 10 sec. Then, an aqueous solution of dextran (5 g in 10 ml water) was added to the mixture and stirred for 1 hr. Finally, the entire mixture was centrifuged for 30 minutes to remove large particles, whereas the supernatant was collected, filtered, and washed several times with distilled water through an Amicon cell (Millipore ultrafiltration membrane YM-30 k) to remove any free dextran molecules.

Figure 3:
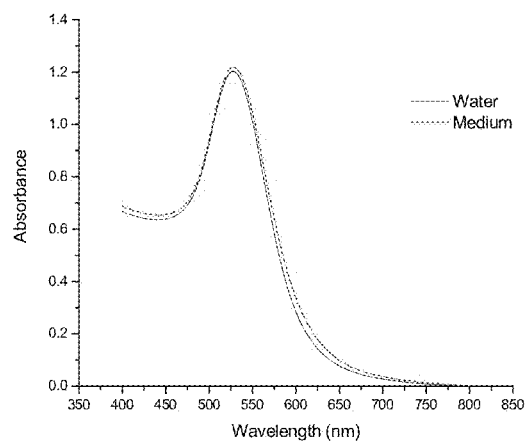
FIG. 3 illustrates the UV-Visible spectra of gold nanoparticles in non-assembled conditions.

Dextran-Coated Gold Nanoparticles for Antimicrobial Susceptibility:

In order to determine if noble metal nanoparticles, like Au NPs', surface plasmon resonance band is affected by the presence of complex growing media, we added into the nanoparticle suspension (400 μL Au NPs in 600 μL distilled water) either 10 μL distilled water (black line) or 10 μL Mueller-Hintro (MH) broth containing starch (red line). After examination of the samples on a Cary 300 UV-Visible spectrophotometer (Varian Inc.), both samples exhibited the same surface plasmon peak (FIG. 3). This supported the hypothesis that the nanoparticles' surface plasmon band would not be affected by the presence of media, under non-assembled conditions.

Figure 4:
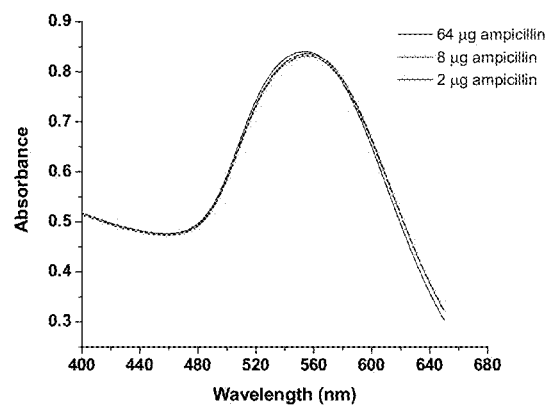
FIG. 4 depicts that AuNPs' spectral characteristics are independent of the antibiotic concentration, under Concanavalin A-induced clustering.

Subsequently, we determined if the presence of antibiotics in the growing media had any effects on the shift of the surface plasmon band, under assembled conditions. Specifically, 10 μL aliquots of MH broth, with varying amounts of ampicillin, were incubated with gold nanoparticles (400 μL Au NPs in 600 μL distilled water) for 30 minutes at room temperature in the presence of 10 μL Concanavalin A (1 μg/μL). The samples were examined on a Cary 300 UV-Vis spectrophotometer, and the shift of the surface plasmon band was determined. The obtained data indicated that the shift of the surface plasmon resonance band is independent of the antibiotic's concentration, under concanavalin-induced assembled conditions (FIG. 4).

Figure 5:
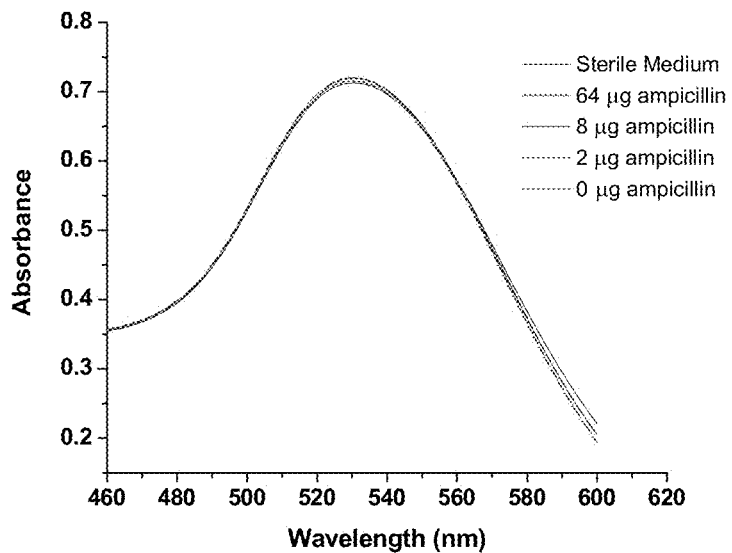
FIG. 5 shows that in the absence of ConA, the AuNPs were in a non-assembled state, exhibiting the same spectral characteristics, regardless of the presence of bacteria and antibiotic; samples with ampicillin (64, 8, and 2 µg) and the bacterial growth control (0 µg ampicillin) contained aliquots from liquid cultures initially inoculated with $10^6$ CFU of E. coli.

Considering that Con A has affinity towards molecules with carbohydrate moieties, we reasoned that any variations in the carbohydrate concentrations should be observable using a known amount of dextran-coated nanoparticles and Con A, based on the surface plasmon band shift. Hence, the shift of the gold nanoparticles' surface plasmon resonance band should have depended on bacterial metabolism and corresponded to the levels of free carbohydrates in the solution. To study this, E. coli ($10^6$ CFU) were incubated for 2 hours at 37° C. in MH broth, in the presence of various concentrations of ampicillin. Then, 10 μL aliquots of these samples were added into the Au NPs suspension, as stated above. Despite the presence of bacteria and antibiotic, the samples exhibited identical absorption spectra, under non-assembled conditions (FIG. 5).

Figure 6:
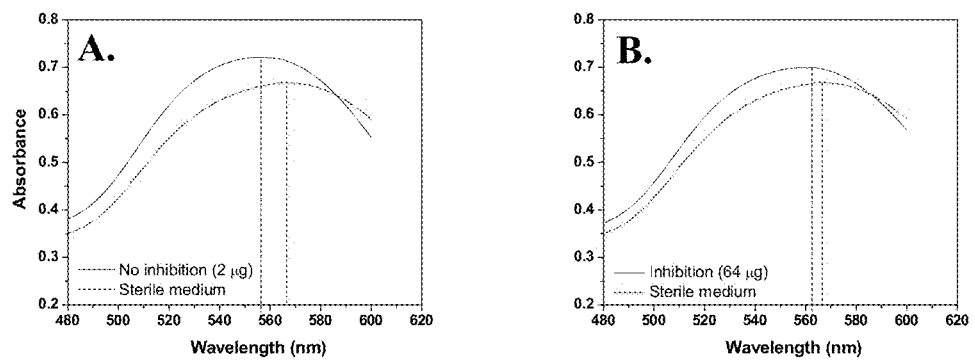
FIG. 6 presents the shift of the gold nanoparticles' surface plasmon band at (A) low (non-inhibitory, 2 µg) and (B) high (inhibitory, 64 µg) ampicillin concentrations.
Figure 7:
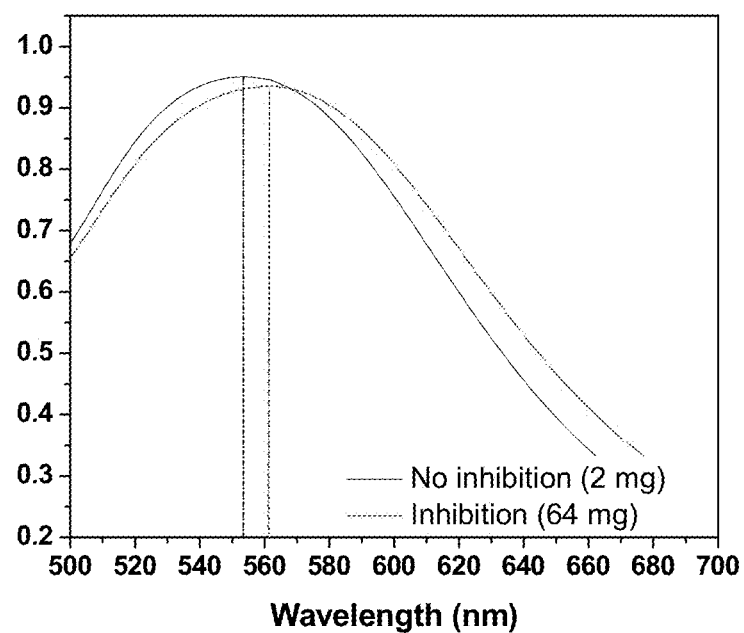
FIG. 7 shows the shift of the gold nanoparticles' surface plasmon band at low (non-inhibitory, 2 µg) and high (inhibitory, 64 µg) ampicillin concentrations, while using higher amount of AuNPs (50:50 AuNP:dH2O v:v)

After addition of Con A and a 30-minute incubation at 25° C., distinct spectral differences were observed. Interestingly, under a small, presumably non-inhibitory, antibiotic concentration the shift in the band was low, compared to the sterile control (FIG. 6A). A similar trend was also observed in the sample where bacteria grew in the absence of the antibiotic. However, under high, most likely inhibitory, concentration the shift was large with a broader shoulder, resembling the sterile control (FIG. 6B). This behavior was due to the higher amount of free carbohydrates that have not been utilized by the bacteria as their metabolism was suppressed, promoting extensive concanavalin-induced Au NP clustering. Analogous results were obtained when higher concentrations of Au NPs were used (FIG. 7).

Figure 8:
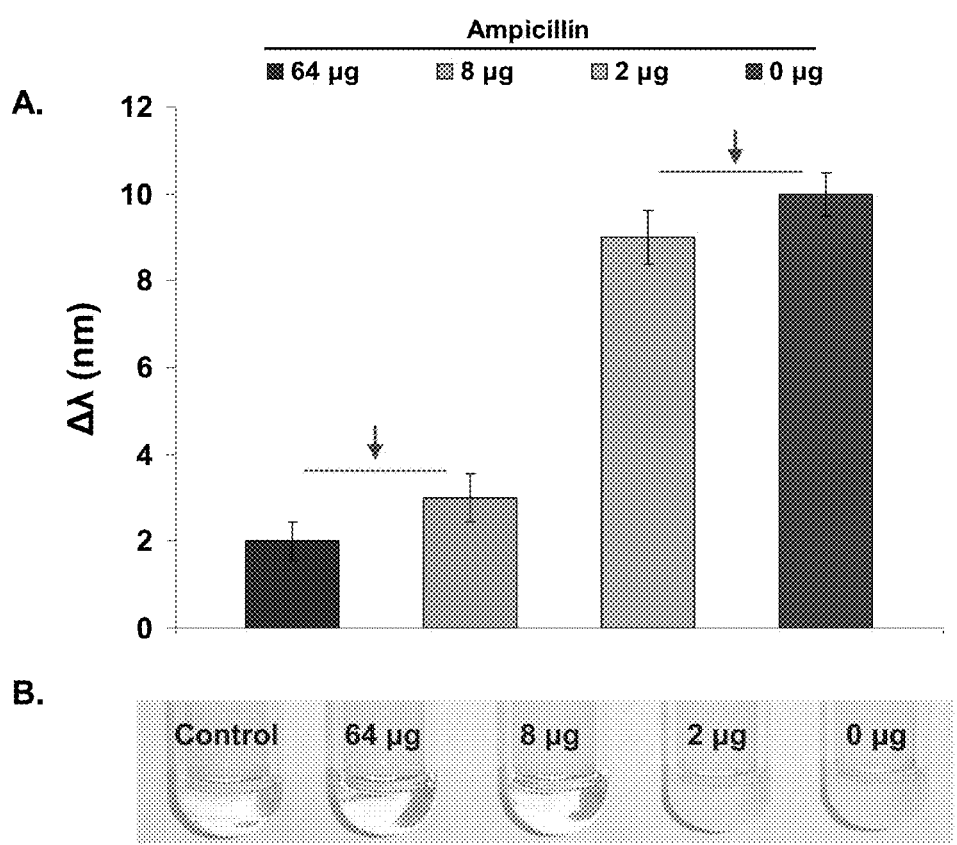
FIG. 8 is a determination of the MIC using (A) the surface plasmon peak shift of Au NPs and (B) the turbidity method (original photograph, numbers indicate the amount of ampicillin)

Accurate determination of the minimum inhibitory concentration (MIC) can prevent adverse side effects, such as renal toxicity. Considering that the contemporary MIC determination depends on a day-long process, we examined if Au NPs can yield results faster without sacrificing reliability. Initially, E. coli ($10^6$ CFU) were incubated for 2 hours at 37° C. in MH broth, in the presence of different concentrations of ampicillin. Then, aliquots of these samples were incubated with Au NPs for 30 minutes at 25° C., in the presence of Con A. Based on the shifts of the surface plasmon band, the MIC was determined to be 8 μg, as the corresponding surface plasmon band shift was statistically different than the control, containing bacteria growing in the absence of antibiotic (FIG. 8A). Correlation with standard methods was achieved by inoculating serial dilutions of ampicillin in MH broth with E. coli, followed by a 24-hour long incubation at 37° C. Bacterial growth was assessed based on the broth's turbidity, whereas absence of turbidity was an indicator of successful antimicrobial susceptibility. The lowest ampicillin concentration where the MH broth was clear, suggesting that no bacteria proliferated, was 8 μg (FIG. 8B). This concentration was identical to the Au NP-determined MIC, though the Au NP-based method yielded the same results much faster.

Figure 9:
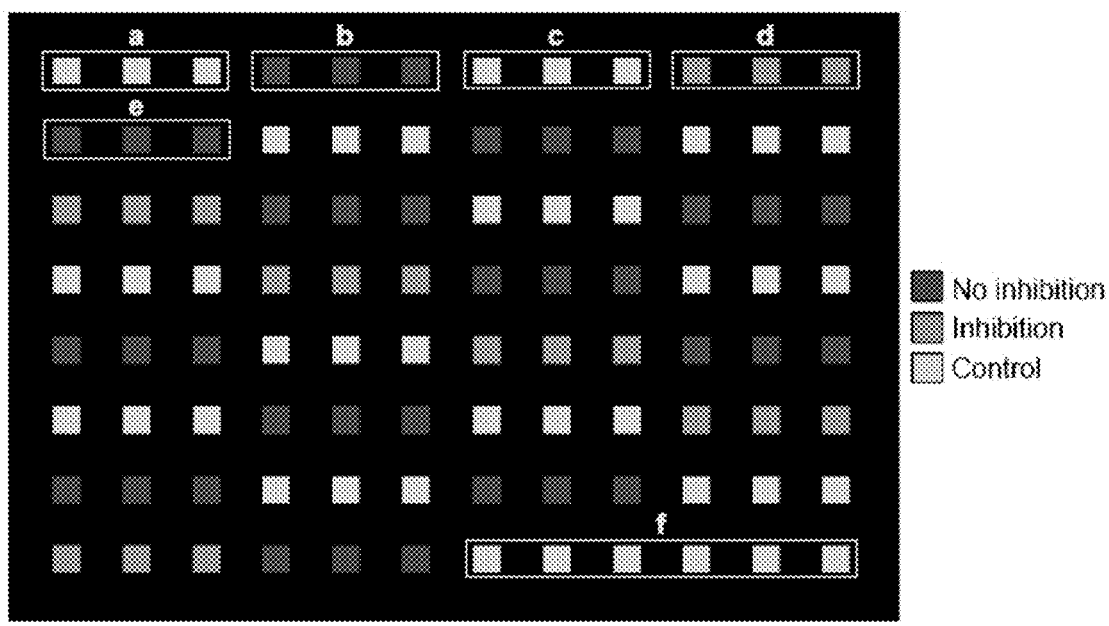
FIG. 9 is a determination of MIC in high-throughput format using Au-NP and ConA; purple squares indicate absence of bacterial metabolism, green areas demonstrate inhibition of bacterial metabolism, and red wells show active bacterial metabolism, similar to the data trend of Table 1; Group (a) Sterile Mueller-Hinton (MH) broth, (b) E. coli ($10^6$ CFU) grown in the absence of ampicillin, (c) heat-inactivated E. coli ($10^6$ CFU) in MH broth, (d) and (e) E. coli ($10^6$ CFU) grown in the presence of 64 and 2 µg ampicillin, respectively; following wells include replications of these groups, obeying the above pattern; Group (f) consists of additional control samples, similar to (a)

Finally, the potential of our Au-NP-based assay for the determination of antimicrobial susceptibility in high-throughput format was investigated. In these studies, samples of heat-inactivated *E. coli* ($10^6$ CFU) and *E. coli* ($10^6$ CFU) grown in the presence or absence of ampicillin were screened with the Au-NP on a 96-well plate using a microtiter plate reader. Addition of Con A, followed by a 30-min incubation at 25° C., resulted in distinct changes of the surface plasmon band, similar to those described above (FIG. 8A) with standard errors of less than 0.6 nm. This allowed the categorization of the samples in inhibitory (heat-inactivation and 64 µg ampicillin) or non-inhibitory (2 and 0 µg ampicillin) cohorts (FIG. 9), demonstrating the capability of our method to screen multiple samples and assess various compounds' antimicrobial activity simultaneously in a high-throughput format.

Figure 10:
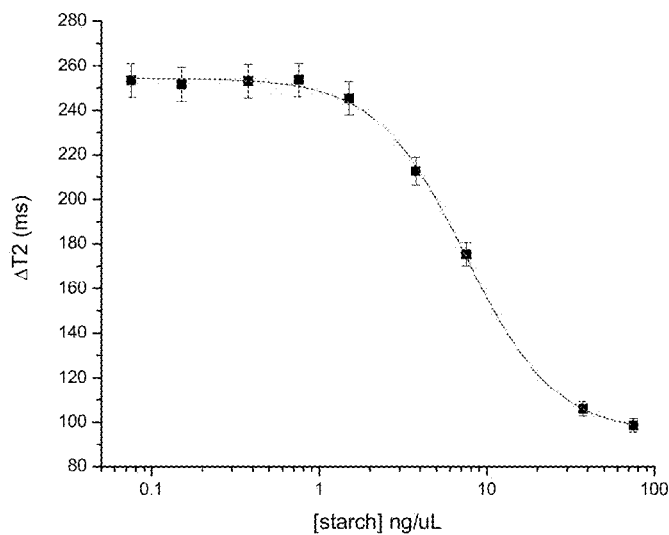
FIG. 10 shows dose-dependent changes in T2 of dextran-coated IONPs in the presence of Con A after a 30-minute incubation at room temperature; sigmoidal fit was applied with an R2=0.99 (OriginPro 7.5); similar results were obtained after 0-, 90- and 150-minute incubations.

Dextran-Coated Iron Oxide Nanoparticles for Antimicrobial Susceptibility:

First, we wanted to determine if magnetic IO NPs coated with dextran could be used to determine and quantify the levels of a polysaccharide (starch) in bacterial culture media. Specifically, 190 µl of IO NPs (9.5 µL nanoparticles [0.685 µg Fe/µL] in 180.5 µL deionized water) were inoculated with 10 µL specimens of starch-containing growth media. Ten µL of Concanavalin A (1 µg/µL) were added, and then the samples were incubated at room temperature for various time intervals. The samples were examined in a Bruker 0.47 T (20 MHz) magnetic relaxometer (The MiniSpec, Bruker), and the individual sample's changes in spin-spin relaxation times ($\Delta T2$) were determined based on the formula: $|\Delta T2_{incubation\ time} - \Delta T2_{prior\ ConA}|$. The obtained data indicated that the changes in $\Delta T2$ depend on the starch concentration, under concanavalin-induced assembled conditions (FIG. 10). The observed behavior supported the hypothesis that magnetic nanoparticles affect the spin-spin relaxation times of adjacent water protons in a dose-dependent manner, associated with the levels of carbohydrates within a solution, under assembled conditions.

Figure 11:
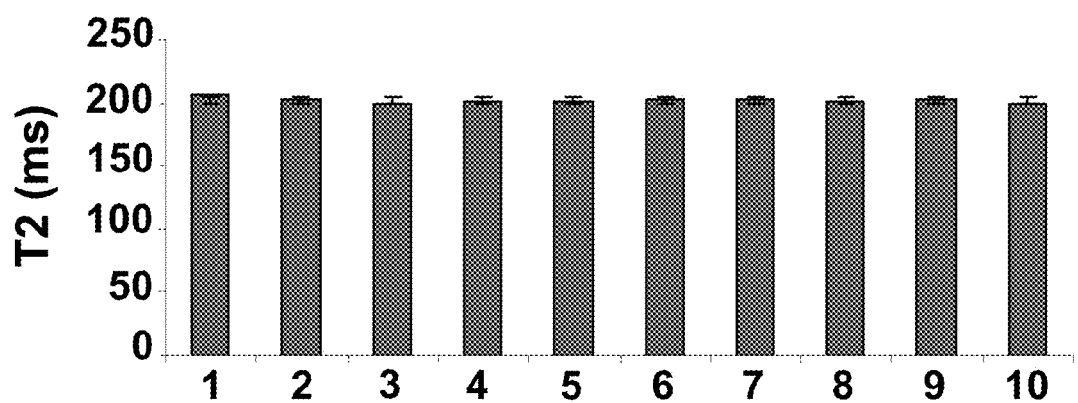
FIG. 11 shows that in the absence of ConA, the IO NPs were in a non-assembled state, exhibiting the same T2, regardless of the presence of bacteria. 1; water, 2; sterile medium (with starch), 3; sterile medium (no starch), 4; $10^2$ CFU of *E. coli*, 5; $10^3$ CFU of *E. coli*, 6; $10^4$ CFU of *E. coli*, 7; $10^5$ CFU of *E. coli*, 8; $10^6$ CFU of *E. coli*, 9; $10^8$ CFU of *E. coli*, 10; $10^9$ CFU of *E. coli*.
Figure 12:
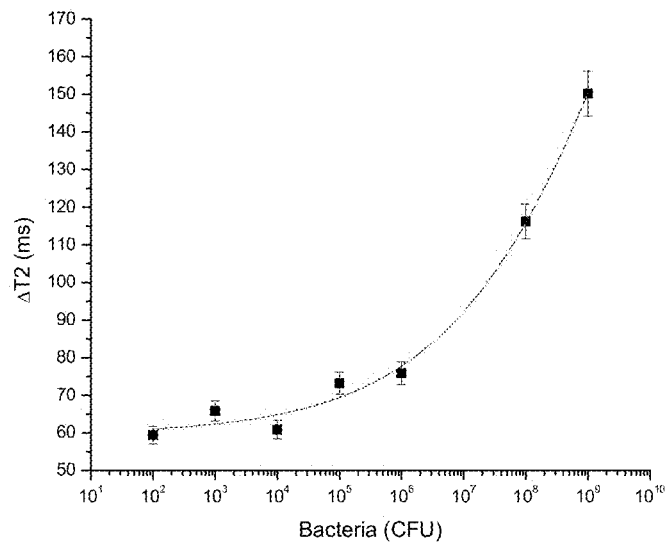
FIG. 12 shows dose-dependent changes in T2 of IONPs associated with starch consumption, due to various degrees of bacterial loads; the graph depicts data obtained after a 30-minute incubation at room temperature, in the presence of Concanavalin A; sigmoidal fit was applied with an R2=0.99 (OriginPro 7.5); similar results were obtained after 0- and 90-minute incubations.

Next, as bacteria utilize carbohydrates in their metabolic pathways, we hypothesized that any variations in the carbohydrate concentrations attributed to bacterial growth should be observable, using a known amount of dextran-coated IO NPs and Con A. Hence, the changes in T2 of the nanoparticles' suspension should have been related to the extent of carbohydrates consumption by bacteria. Therefore, the more bacteria present in a suspension the higher the consumption and depletion of carbohydrates should have been. In order to test this hypothesis, samples of various CFU loads of log-phase *E. coli* were incubated for 1 hour at 37° C. in MH broth, to allow carbohydrate (starch) consumption. Then, the samples were autoclaved, and 10 µl aliquots were added to 190 µL of dextran-coated IO NPs (9.5 µL nanoparticles [0.685 µg Fe/µL] in 180.5 µL deionized water). Before addition of Con A, all samples exhibited the same T2 (FIG. 11). Addition of Con A (1 µg/µL) induced nano-assembly formation, resulting in dose-dependent changes in T2 (FIG. 12). The more pronounced changes (higher $\Delta T2$) were observed in samples with higher bacterial loads, due to the higher, more extensive consumption of starch.

Figure 13:
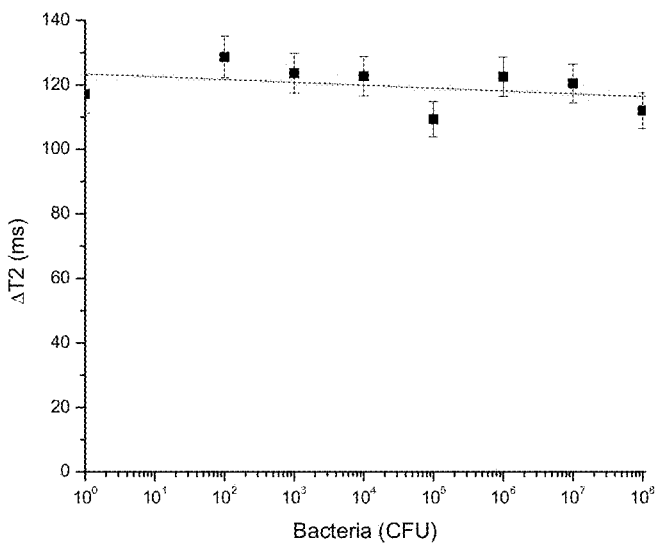
FIG. 13 depicts that the behavior of IONPs is independent of the bacterial population, but it is dependent of active bacterial metabolism; the graph depicts data obtained after a 30-minute incubation at room temperature, in the presence of Con A; linear fit was applied with an R2=0.14 (OriginPro 7.5); similar results were obtained after 0-, 90- and 150-minute incubations.

In order to determine if indeed the observed differences were attributed to the consumption of starch, and not to the populations of bacteria present per se, we incubated various amounts of *E. coli* in MH broth with 1.5 mg/mL starch concentration, for 10 minutes at 37° C., in order to prevent bacterial cell division. Immediately after incubation, the samples were autoclaved, in order to heat inactivate the bacteria and halt their metabolic reactions. Then, 10 µL aliquots of these samples were incubated with IO NPs, as described above. Addition of Con A (1 µg/µL) resulted in nanoassembly formation, yet with no statistically significant differences (FIG. 13). Considering these data, we concluded that the nanoparticle technology can sense the starch levels and bacterial metabolism, and not the bacteria per se.

Figure 14:
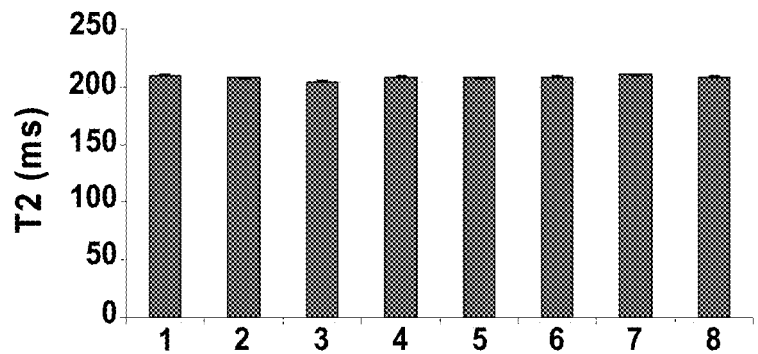
FIG. 14 indicates that in the absence of ConA, the IONPs exhibited the same T2, regardless of the presence of bacteria and antibiotic, 1; water, 2; sterile medium (with starch), 3; sterile medium (no starch), 4; 64 µg ampicillin, 5; 8 µg ampicillin, 6; 2 µg ampicillin; 7; 1 µg ampicillin, 8; 0 µg ampicillin.
Figure 15:
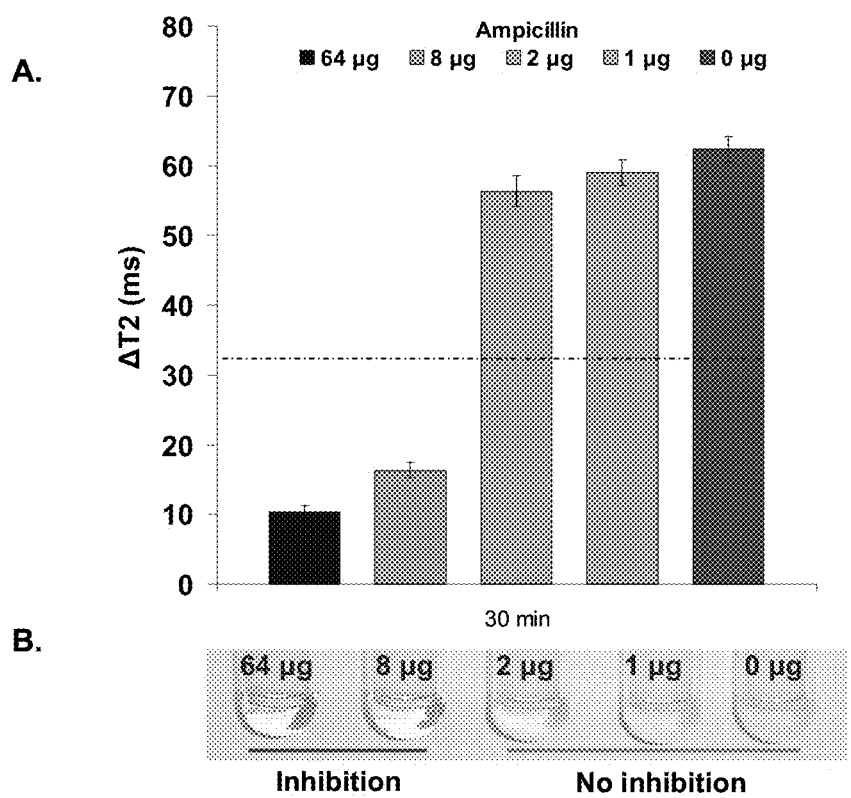
FIG. 15 is a determination of the minimum inhibitory concentration using (A) the changes in spin-spin relaxation times (ΔT2) and (B) the turbidity method (original photograph, numbers indicate the amount of ampicillin); a similar trend was observed after 0- and 45-minute incubation at room temperature; the dotted line indicates the threshold of the drug's successful inhibition.

Then, utilizing the IO NPs, we determined ampicillin's MIC. Specifically, *E. coli* ($10^6$ CFUs) were incubated for 2 hours at 37° C. in MH broth, in the presence of different concentrations of ampicillin. Then, 10 µL specimens of these samples were incubated with IO NPs, as described above. In the absence of Con A, all samples had identical T2 values, indicating that the presence of bacteria and antibiotic does not affect the spin-spin relaxation time of the nanoparticle suspension (FIG. 14). However, in the presence of Con A and after a 30-minute incubation at room temperature, distinct changes were observed (FIG. 15A). Specifically, the magnetic-relaxation-determined minimum inhibitory concentration was 8 µg, as at this concentration we observed a drastic change in the values of $\Delta T2$. Confirmation of the T2-derived minimum inhibitory concentration was achieved through the turbidity test, described before. Notably, both the T2- and turbidity-derived concentrations were identical (FIG. 15B).

Figure 16:
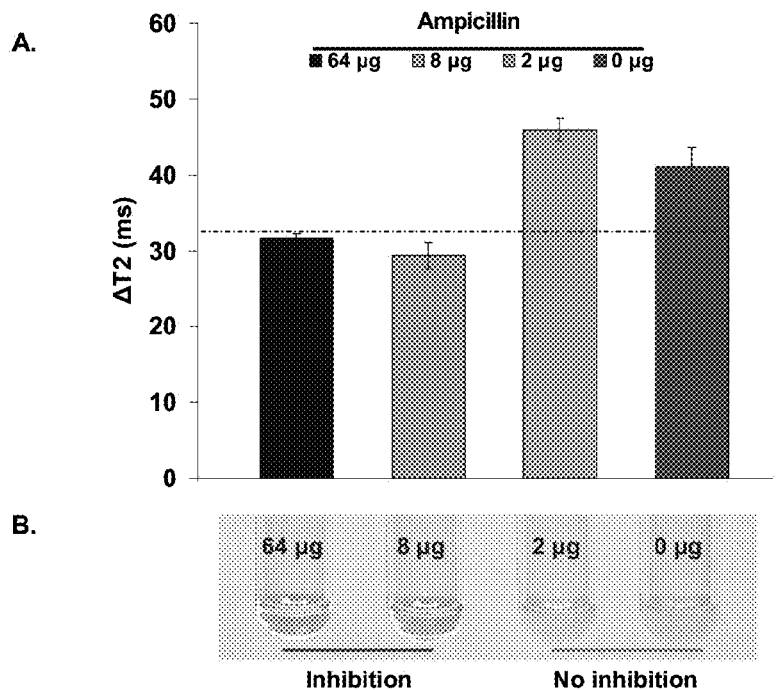
FIG. 16 is a determination of the minimum inhibitory concentration of *Shigella sonnei* using the changes in spin-spin relaxation times (ΔT2) after a 30-min incubation at 25° C.; the dotted line indicates the threshold of the drug's successful inhibition.
Figure 17:
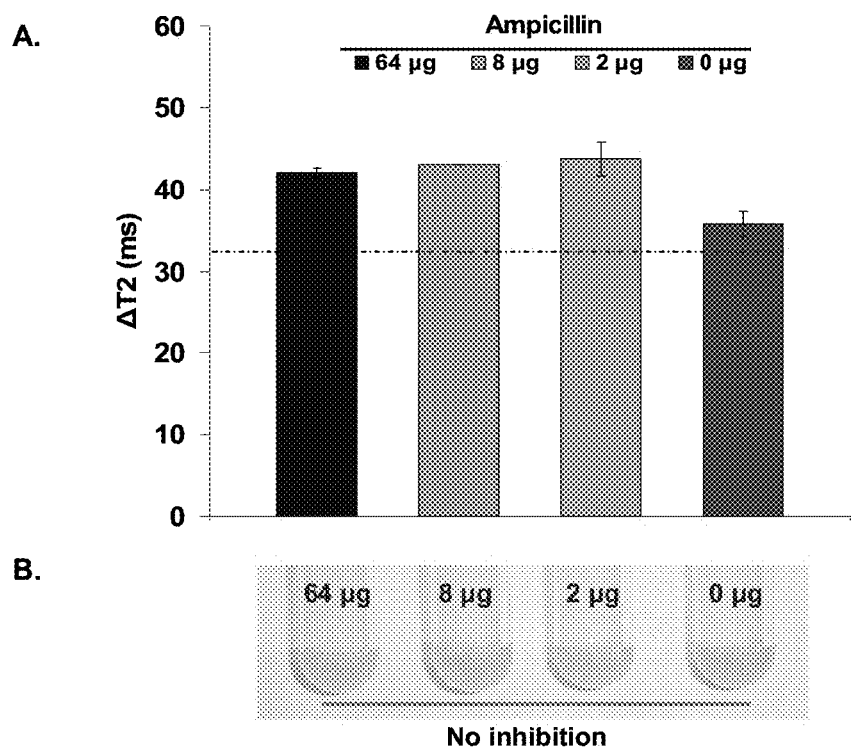
FIG. 17 shows an assay of antibiotic resistance of *Serratia marcescens* using the changes in spin-spin relaxation times (ΔT2) after a 30-min incubation at 25° C.; the dotted line indicates the threshold of the drug's successful inhibition.

We then determined the antibiotic susceptibility or resistance of other bacteria utilizing the IO NPs. *Shigella sonnei* ($10^6$ CFUs) and *Serratia marcescens* ($10^6$ CFUs), grown in pure cultures, were incubated for 2 hours at 37° C. in MH broth, in the presence of different concentrations of ampicillin. Ten µL specimens of these samples were incubated with IO NPs, as described above. In the absence of Con A, all samples had identical T2 values. Addition of Con A, followed by a 30-minute incubation at room temperature, resulted in different patterns between the two microorganisms (FIGS. 16 and 17). Specifically, the magnetic-relaxation-determined minimum inhibitory concentration was 8 µg for *Shigella sonnei* (FIG. 16), whereas *Serratia marcescens* was found to be resistant to ampicillin, as all samples exhibited similar changes in the T2 (FIG. 17). Confirmation of the T2-derived minimum inhibitory concentration was achieved through the turbidity test, yielding identical results to the T2-mediated ones.

Lastly, due to the fact that many bacteria can either cause septicemia or require growth in optically turbid media, it is important to assess bacterial susceptibility in these complex matrices. However, most current methods cannot be utilized for the detection of molecular targets and assessment of antimicrobial susceptibility in blood, due to the strong absorbance and scattering from the matrix's constituents, including platelets and red blood cells. Therefore, considering these drawbacks and the facts that bacterial isolation is a major limitation step in diagnosis and that certain pathogenic microorganisms require growth in specialized media, we investigated whether the dextran-coated polysaccharide nanosensors could assess antimicrobial susceptibility in blood. Recently, we reported the high-throughput bacterial susceptibility determination, using the surface plasmon band shifts of gold nanoparticles. However, this method cannot be used in opaque media, such as blood, due to the intrinsic optical properties of the matrix, masking the nanoparticles' plasmonic band. To investigate this, we used *E. coli* and *S. marcescens* cultures suspended in blood-supplemented MH broth and incubated in the presence of ampicillin for 2 hours at 37° C. Aliquots of these cultures (10 µL) were obtained and added into the dextran-coated polysaccharide nanosensors working solution, followed by 10 µL Con A treatment (1 µg/µL). After 45 minutes following Con A addition at room temperature, we determined that the *E. coli's* ampicillin MIC was 8 μg, without observing any nanoparticle precipitation. Additionally, the *S. marcescens*' drug resistance was identified after an hour-long incubation at 25° C. These data were published in the above-referenced paper in *Plos One*, September 2008, Vol. 3, Issue 9, e3253;an Internet publication available at www.plosone.org.

Figure 18:
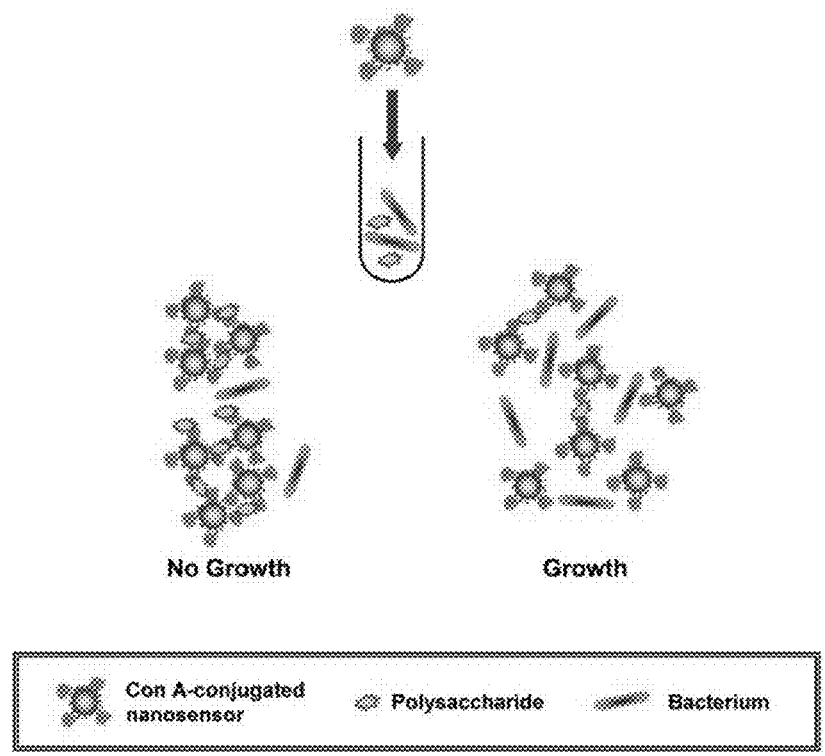
FIG. 18 shows a schematic representation of the assessment of antimicrobial susceptibility using Concanavalin A-conjugated polysaccharide nanosensors using a silica coating where the direct conjugation of Con A to the capping matrix results in a non-competition based assay format.

Antimicrobial Susceptibility Assessment Using Concanavalin A-Conjugated Polysaccharide Nanosensors Often times a slight modification in the nanosensors' design and/or the protocol followed can result in significant improvements in either the sensitivity or speed of the assay. Therefore, we hypothesized whether conjugating Con A to the surface of the magnetic nanoparticles would allow for faster kinetics and shorter the detection time. For these experiments, we conjugated Con A directly to aminated silica-coated iron oxide nanoparticles. We chose silica-coated instead of dextran-coated iron oxide nanoparticles to avoid possible cross reaction with the dextran on the nanoparticle's surface. In this non-competition assay (FIG. 18), the Con A-conjugated silica coated nanosensors would facilitate the direct sensing of the levels of carbohydrates in solution, as opposed to the competition assay that requires two reagents; the dextran-coated nanoparticles and the Con A for successful sensing. The aminated silica-coated nanoparticles were synthesized using a modified water-based synthetic protocol. The resulting nanoparticles were monodispersed, having a diameter of 145 nm and an R2 relaxivity of 225 $mM^{-1}s^{-1}$.

Figure 19:
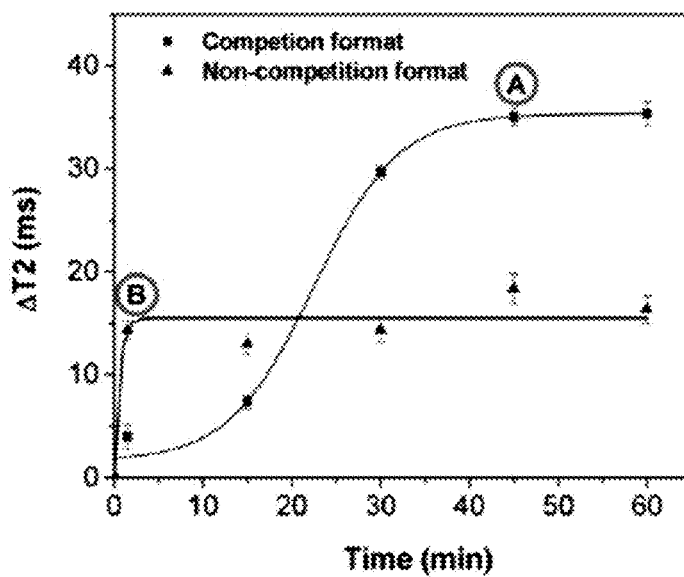
FIG. 19 shows kinetic profiles of the dextran-coated nanosensors and Con-A conjugated nanosensors where point A is the end-point of the dextran-coated nanosensors and point B is the end-point of of the Con-A conjugated nanosensors.

In our first set of experiments with the aminated silica-coated nanoparticles, we determined whether these nanoparticles clustered non-specifically in the presence of Con A in solution. As expected, we observed that Con A did not induce any changes in the relaxation times of the nanoparticles. This demonstrates that the silica coating on these nanoparticles lacks any carbohydrate epitopes, rendering them suitable for the noncompetition-based sensing of carbohydrates. Therefore, we conjugated Con A to the aminated silica-coated nanoparticles, via carbodiimide chemistry, resulting in Con A-carrying nanoparticles with a hydrodynamic diameter of, 160 nm (R2=225 $mM^{-1}s^{-1}$, [Con A]=0.03 μg/μL). First, we compared the kinetic profiles of the dextran-coated nanosensors and Con A-conjugated nanosensors using bacterial *E. coli* blood cultures (106 CFU grown in the presence of 2 μg ampicillin). Interestingly, we found that the non-competition assay with the Con A-conjugated nanosensors (FIG. 19, curve B) provided faster results than the competition assay that utilizes the dextran-coated nanosensors (FIG. 19, curve A). Specifically, the competition assay format reached its end-point after a 45-minute incubation, whereas the non-competition assay reaches its end-point within 5 minutes upon addition of the bacterial sample. These findings support our hypothesis of achieving faster kinetics due to the direct conjugation of Con A to the nanoparticles.

Figure 20:
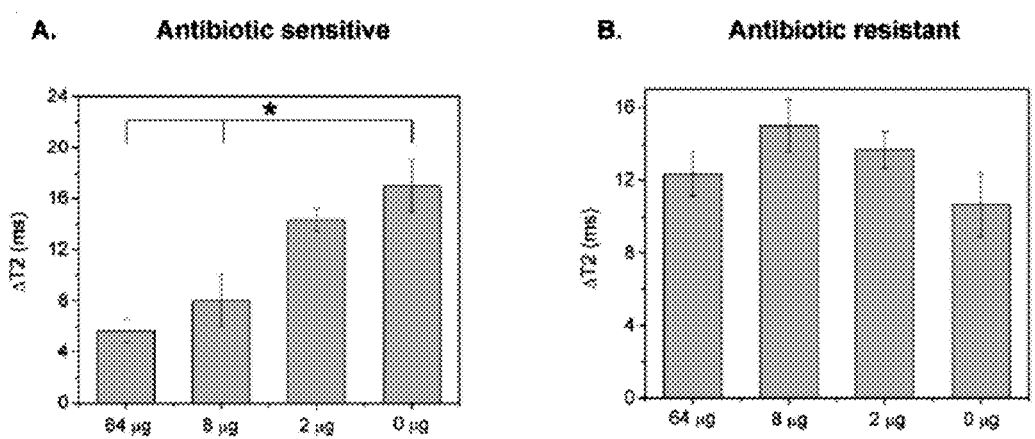
FIG. 20 shows the antimicrobial susceptibility in blood using Con-A conjugated nanosensors in which (A) is a graph of the determination of *E Coli's* ampicillin MIC in blood and (B) is a graph of the determination of *Serratia marcescens*' drug resistance in blood with the Con-A conjugated nanosensors five minutes after addition of a bacterial aliquot into the nanoparticle solution (Means±SE; p<0.05).

Then, we examined if MIC determination can be achieved using these Con A-conjugated nanosensors, in blood cultures of *E. coli* and *S. marcescens*. Immediately upon addition of the bacterial sample into the nanoparticle solution, distinct changes in the T2 were observed. Specifically, within 5 minutes the Con A nanosensors were able to determine that *E. coli* had an ampicillin MIC of 8 μg (FIG. 20A), in line with the data from the dextrancoated nanosensors in the competition assay or the turbidity test. Likewise, within 5 minutes the Con A-conjugated nanosensors assessed that *S. marcescens* was resistant to ampicillin, further corroborating the findings that the non-competition assay format provides faster results than the competition-based assay of the dextran-coated nanosensors (FIG. 20B).

The Con A-conjugated polysaccharide nanosensor assay yields faster results, without compromising sensitivity and reliability, due to faster binding kinetics. Also, as there is no need for the addition of a second reagent (Con A), this format might be particularly useful for point of-care diagnostics and applications in the field.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A method of testing bacterial cells for antimicrobial susceptibility, the method comprising:
   mixing a suspension of bacterial cells in a non-nutrient medium with an antimicrobial and a carbohydrate usable by the bacterial cells;
   adding iron oxide nanoparticles and a lectin to the mixture; and
   monitoring a parameter associated with the nanoparticles responsive to use of the carbohydrate by the bacterial cells.

2. The method of claim 1, wherein the antimicrobial comprises a pharmaceutical administrable to a human or animal patient.

3. The method of claim 1, wherein the iron oxide nanoparticles nanoparticles comprise rod-shaped nanoparticles.

4. The method of claim 1, wherein the lectin is conjugated to the surface of the iron oxide nanoparticles before adding.

5. The method of claim 1, wherein the iron oxide nanoparticles further comprise a coating polymer which bears the lectin.

6. The method of claim 1, wherein the iron oxide nanoparticles further comprise a coating of amino-silica bearing the lectin.

7. The method of claim 1, wherein the iron oxide nanoparticles further comprise a coating polyacrylic acid polymer bearing the lectin.

8. The method of claim 1, wherein the lectin has a high binding affinity for the carbohydrate.

9. The method of claim 1, wherein the lectin comprises concanavalin A.

10. The method of claim 1, wherein the parameter is monitored by nuclear magnetic resonance.

11. The method of claim 1, wherein the parameter is monitored by the nuclear magnetic resonance T2 water relaxation time.

12. The method of claim 1, wherein the magnetic relaxation parameter comprises an increase or a decrease in T2 water relaxation time by nuclear magnetic resonance.

13. The method of claim 1, wherein the iron oxide nanoparticles are capable of causing an increase or a decrease in the T2 of water.

* * * * *